United States Patent
Lancelle et al.

(10) Patent No.: US 10,980,621 B2
(45) Date of Patent: Apr. 20, 2021

(54) DENTAL DESIGN TRANSFER

(71) Applicant: Ivoclar Vivadent AG, Schaan (LI)

(72) Inventors: Marcel Lancelle, Zürich (CH); Roland Mörzinger, Zürich (CH); Nicolas Degen, Erlenbach (CH); Gabor Sörös, Zürich (CH); Bartolovic Nemanja, Zürich (CH)

(73) Assignee: Ivoclar Vivadent AG, Schaan (LI)

( * ) Notice: Subject to any disclaimer, the term of this patent is extended or adjusted under 35 U.S.C. 154(b) by 121 days.

(21) Appl. No.: 16/279,166

(22) Filed: Feb. 19, 2019

(65) Prior Publication Data
US 2019/0254789 A1 Aug. 22, 2019

(30) Foreign Application Priority Data

Feb. 20, 2018 (EP) .................................. 18157574
Feb. 21, 2018 (EP) .................................. 18157809
Sep. 28, 2018 (EP) .................................. 18197512

(51) Int. Cl.
| | |
|---|---|
| *A61C 13/34* | (2006.01) |
| *A61C 5/77* | (2017.01) |
| *A61C 9/00* | (2006.01) |
| *A61C 13/00* | (2006.01) |
| *A61B 90/00* | (2016.01) |

(Continued)

(52) U.S. Cl.
CPC .............. *A61C 13/34* (2013.01); *A61B 90/36* (2016.02); *A61C 5/77* (2017.02); *A61C 9/004* (2013.01); *A61C 9/0046* (2013.01); *A61C 9/0053* (2013.01); *A61C 13/0019* (2013.01); *G06T 17/20* (2013.01); *G06T 19/20* (2013.01); *G16H 30/40* (2018.01); *A61B 5/4547* (2013.01); *A61B 2090/365* (2016.02); *A61C 7/002* (2013.01); *A61C 13/0004* (2013.01); *B33Y 80/00* (2014.12); *G06T 2207/30036* (2013.01); *G06T 2210/41* (2013.01); *G06T 2219/2016* (2013.01);

(Continued)

(58) Field of Classification Search
USPC .......................................................... 382/154
See application file for complete search history.

(56) References Cited

U.S. PATENT DOCUMENTS

| | | | |
|---|---|---|---|
| 7,717,708 B2 | 5/2010 | Sachdeva | |
| 9,585,549 B1 * | 3/2017 | Elazar | .................... A61B 5/067 |

(Continued)

FOREIGN PATENT DOCUMENTS

| | | | | |
|---|---|---|---|---|
| WO | WO 2018112273 | * | 6/2018 | ............. A61B 90/00 |

OTHER PUBLICATIONS

Kapanu, "Augmented Reality for the Future of Dentistry," YouTube, https://www.youtube.com/watch?=cIEXAIN_QF4, Mar. 6, 2017, Zurich, Switzerland.

(Continued)

*Primary Examiner* — Jerome Grant, II
(74) *Attorney, Agent, or Firm* — Ann M. Knab; Thad McMurray (57) ABSTRACT

The invention pertains to a method for exporting design data of a virtual 3D dental design model (12) from an AR application, the AR application being adapted to visualize the dental design model with a preliminary pose and scale (13) in an image (11) of a face comprising a mouth region with a dental situation. The invention further pertains to a method for visualizing a 3D dental design model in an AR application.

13 Claims, 6 Drawing Sheets

(51) Int. Cl.
    *G16H 30/40*     (2018.01)
    *G06T 17/20*     (2006.01)
    *G06T 19/20*     (2011.01)
    *A61C 7/00*     (2006.01)
    *B33Y 80/00*     (2015.01)
    *G16H 50/50*     (2018.01)
    *A61B 5/00*     (2006.01)

(52) U.S. Cl.
    CPC ...... *G06T 2219/2021* (2013.01); *G16H 50/50* (2018.01)

(56) References Cited

U.S. PATENT DOCUMENTS

| | | | |
|---|---|---|---|
| 9,775,491 B2 | 10/2017 | Clausen | |
| 2011/0212420 A1 | 9/2011 | Vuillemot | |
| 2013/0060532 A1 | 3/2013 | Clausen | |
| 2013/0158958 A1 | 6/2013 | Methot | |
| 2013/0218530 A1 | 8/2013 | Deichmann et al. | |
| 2016/0188277 A1* | 6/2016 | Miyasaka | G06F 3/1438 345/2.2 |
| 2017/0319293 A1 | 11/2017 | Fisker | |
| 2018/0153659 A1 | 6/2018 | Fisker et al. | |
| 2018/0168781 A1 | 6/2018 | Kopelman et al. | |
| 2019/0117337 A1* | 4/2019 | Tsai | G06T 11/60 |
| 2019/0254790 A1* | 8/2019 | Lancelle | A61C 13/34 |
| 2019/0254791 A1* | 8/2019 | Lancelle | G16H 30/40 |
| 2019/0259220 A1* | 8/2019 | Lancelle | G06T 15/04 |
| 2019/0269482 A1* | 9/2019 | Shanjani | G06F 3/013 |
| 2019/0269485 A1* | 9/2019 | Elbaz | A61B 5/0059 |
| 2019/0290408 A1* | 9/2019 | Fisker | A61C 11/00 |
| 2020/0043663 A1* | 2/2020 | Kim | H01G 4/012 |
| 2020/0066391 A1* | 2/2020 | Sachdeva | G16H 20/40 |
| 2020/0107915 A1* | 4/2020 | Roschin | A61C 9/0053 |
| 2020/0143541 A1* | 5/2020 | Wang | A61C 7/002 |
| 2020/0155276 A1* | 5/2020 | Cam | A61C 7/08 |
| 2020/0222156 A1* | 7/2020 | Kopelman | A61C 19/045 |

OTHER PUBLICATIONS

Amirkhanov, Aleksandr et al., "WithTeeth: Denture Preview in Augmented Reality," Eurographics Proceedings, The Eurographics Association, pp. 1-10, 2018.

* cited by examiner

DENTAL DESIGN TRANSFER

CROSS-REFERENCE TO RELATED APPLICATIONS

This application claims priority to European patent application No. 18197512.9 filed on Sep. 28, 2018, European patent application No. 18157574.7 filed on Feb. 20, 2018, and European patent application No. 18157809.7 filed on Feb. 21, 2018, all the disclosures of which are incorporated herein by reference in their entirety.

TECHNICAL FIELD

The present invention pertains to the field of dental augmented reality applications and more specifically to computer-implemented methods that allows transferring data of a three-dimensional dental design model designed using an augmented reality (AR) application to another, e. g. external, application such as a computer-aided design (CAD) application and—vice versa—transferring a three-dimensional dental design model designed using an orthodontic simulation application or CAD application to an AR application. These methods allow transferring a preliminary design of a dental situation, for instance to plan a dental treatment or to preview the designed situation in the face of a patient.

For dental professionals and patients, it is of interest to get a visual impression of the appearance of the patient's face with a modified dental situation, i.e. to visualize the modified dental situation in an image of the face of the patient. Also, the appearance during or after a dental treatment may be of importance for the patient before deciding to undergo such treatment. For this purpose, a virtual preview (virtual mockup) of the dentition modified by dental treatment is helpful for the dentist and may also be used in the course of interactively modifying the treatment plan to get the most favourable aesthetic results.

In the context of the present invention, the term "denture" is not necessarily restricted to full dentures but also comprises partial dentures, orthodontic situations or adaptations, or dental restorations such as dental prostheses, including crowns, crown lays, veneers, inlays and onlays, bridges, dental implants, and implant restorations. Accordingly, the term "dental model" includes all models of dental prostheses—such as models of complete and partial dentures—that are used for prosthodontic purposes.

BACKGROUND

U.S. Pat. No. 9,775,491 B2, which is hereby incorporated by reference in its entirety, discloses a computer implemented method for visualizing an image rendered from a three-dimensional model of a dental situ-ation to an image of the face of the patient recorded by a camera. In this method a three-dimensional model of the oral cavity of the patient is obtained. This three-dimensional model is modified in a dentistry treatment plan by applying dental restorations to obtain a three-dimensional model of the dental situation of the patient dentition after application of the dental restorations. A two-dimensional image of the face of the patient including the mouth opening is obtained. Then the positioning of the camera that rec-orded the image relative to the dentition of the patient is esti-mated. In this application "positioning of the camera" meant to include the three-dimensional position x, y, z in space and the angular orientation of the camera with respect to the face of the patient. A virtual camera using the estimated positioning is pro-cessing the three-dimensional model of the dental situ-ation to ob-tain a two-dimensional image, and a portion of the three-dimensional model of the dental situation is selected which is visible to the virtual camera. The image rendered by the virtual camera is overlaid and displayed in the image taken by the camera.

Similar methods are set forth in US 2011212420 directed to a method of forming a dental mold, US 20130060532 directed to a method of composing and designing teeth, US 2013158958 directed to a dental analysis method and system, US 20170319293 directed to a method of digitally designing a modified dental setup, and U.S. Pat. No. 7,717,708 directed to computer-based methods for supporting dentists during dental treatment planning for a patient, all of which are hereby incorporated by reference in their entirety.

SUMMARY

It is desirable to create a denture design in an augmented reality application showing the design in the patient's face and then be able to easily export the design to another application such as a computer-aided design application, e.g. to create a denture, restoration or other prosthesis from the design. Likewise, it is desirable to create a denture design in a computer-aided design or orthodontic simulation application and then be able to easily export the design to an augmented reality application to show the design in the patient's face.

It is therefore an object of the present invention to provide an improved method that allows transferring data of a three-dimensional dental design model from an augmented reality application to a computer-aided design application or vice versa.

It is another object to provide such as method wherein a three-dimensional dental design model that has been designed in an augmented reality (AR) application is transferrable to a computer-aided design (CAD) or similar application.

It is a particular object to provide such a method wherein the three-dimensional dental design model transferred to the CAD or similar application can easily be used as a basis to plan a dental treatment.

It is another object to provide such a method wherein a three-dimensional dental design model that has been designed in a CAD application or in an orthodontic simu-lation is transferrable to an AR application.

It is a particular object to provide such a method wherein the three-dimensional dental design model transferred to the AR application can easily be displayed as a preview of a dental situation in the face of a patient.

It is a further object to provide such a method wherein a pose and/or scale of the three-dimensional dental design model is easily adaptable to fit the needs of the receiving AR or CAD application.

It is another object to provide such a method that is performed fully or semi-automatically.

At least one of these objects is achieved by the method of claim 1, the method of claim 9 and/or one of the dependent claims of the present application.

A first aspect of the invention pertains to a computer-implemented method for exporting design data of a virtual three-dimensional dental design model from an augmented reality (AR) application, the AR application being adapted to visualize the dental design model with a preliminary pose and scale in an image of a face comprising a mouth region with a dental situation. The method comprises providing a three-dimensional scan model of the dental situation, aligning the dental situation of the scan model and the dental situation in the image to obtain a pose of the scan model, and calculating, based on the preliminary pose and scale and the pose of the scan model, at least one transformation to bring the design model and the scan model into a common coordinate system.

In particular, the dental design model is brought to a coordinate system of the scan model.

An application to which the design data is exported can be a computer aided design (CAD) application or a similar software, for instance a 3D printer software. This other application can be an external application or an application that is connected to the AR application; for instance, the AR application and a CAD application can be incorporated as sub-applications into the same applications and/or be operatable using the same graphical user interface.

According to one embodiment, the method comprises generating aligned design data based on the transformation, wherein the aligned design data comprises at least a surface geometry of the design model.

According to another embodiment, the method comprises generating aligned design data based on the transformation and obtaining an aligned design model by aligning the design model and the scan model in the common coordinate system, wherein the aligned design data comprises at least a surface geometry of the aligned design model.

According to another embodiment, the method comprises exporting the aligned design data to another application. In particular:

exporting comprises generating an export file comprising the aligned design data;

the aligned design data is exported in a file together with scan model data related to the scan model;

the other application is an external application;

the other application is a CAD application; and/or the export file is in STL file format.

According to another embodiment, the method comprises obtaining an aligned design model, comprising aligning the design model and the scan model in the common coordinate system, and calculating a corrected scale of the dental design model and applying the corrected scale so that the scale of the aligned design model matches the scale of the scan model. In particular, calculating the corrected scale comprises calculating a distance of the dental design model to a virtual camera to match a distance of the scan model to the virtual camera.

According to another embodiment of the method, calculating the transformation comprises applying inverse transformation to the dental design model to maintain visually the same position of the dental design model with respect to the image.

According to another embodiment, the method comprises aligning the scan model to a known coordinate system before determining the pose of the scan model.

In one embodiment, aligning the scan model to the known coordinate system is performed automatically, using heuristics and/or statistical information.

In another embodiment, aligning the scan model to the known coordinate system comprises correcting a scale of the scan model, in particular by orders of magnitudes.

According to a further embodiment of the method, a model based alignment (e. g. edge based alignment) is used for aligning the dental situation of the scan model and the dental situation in the image, the model based alignment comprising at least:

estimating a position of a camera used for capturing the image relative to the face in the image during recording of the image, rendering a two-dimensional image of the scan model using a virtual camera processing the scan model at the estimated position, and carrying out feature detection in the mouth region of the image recorded by the camera and in the rendered image by performing edge detection and/or a colour-based tooth likelihood determination in the respective images and forming a detected feature image for each detected feature.

According to one embodiment of the method, a segmentation of teeth and gum in the scan model is performed using colour information of the scan model and/or using heuristics with position and surface curvature information from the scan model, wherein determining the pose of the scan model is based on the segmentation.

A second aspect of the invention pertains to a computer-implemented method for visualizing a three-dimensional dental design model in an AR application. For instance, the 3D dental design model has been designed or generated in a CAD application, in a deep learning framework or in an orthodontic simulation and is then transferred (imported) from the application in which it has been designed or generated to the AR application to be rendered in an image of a face. The method comprises:

providing the dental design model, a three-dimensional scan model of a dental situation, and an image of a face comprising a mouth region with the dental situation, determining a pose for the dental design model based on the image and on a relative transformation from the scan model to the dental design model, and rendering the dental design model in the image with the determined pose.

According to one embodiment of the method, the dental design model is provided to the AR application by a CAD application or orthodontic simulation.

In one embodiment, the dental design model is designed or modified by a user using the CAD application or orthodontic simulation. In another embodiment, the method comprises designing or modifying the dental design model using the computer-aided design application or orthodontic simulation.

According to one embodiment of the method, determining the pose comprises using a model based alignment (e. g. edge based alignment) for aligning the dental situation of the scan model and the dental situation in the image. This model based alignment can be used especially for further refining the pose and comprises at least:

estimating a position of a camera used for capturing the image relative to the face in the image during recording of the image, rendering a two-dimensional image of the scan model using a virtual camera processing the scan model at the estimated position, and carrying out feature detection in the mouth region of the image recorded by the camera and in the rendered image of the scan model by performing edge detection and/or a colour-based tooth likelihood determination in the images and forming a detected feature image for each detected feature.

According to another embodiment, the method comprises aligning the dental design model and the scan model to a specified coordinate system. In particular, this comprises using a same transformation for the dental design model and the scan model, i.e. in such a way that the dental design model and the scan model stay registered relative to each other.

According to yet another embodiment of the method, a segmentation of teeth and gum in the scan model is performed using colour information of the scan model and/or using heuristics with position and surface curvature information from the scan model, wherein determining the pose of the scan model is based on the segmentation.

According to a further embodiment of the method, colour information is added to the dental design model, wherein determining the pose of the scan model is based on the added colour information. In particular, the colour information is added semi- or fully automatically using statistical information and/or heuristics.

The invention also pertains to a computer programme product comprising programme code which is stored on a machine-readable medium, or being embodied by an electromagnetic wave comprising a programme code segment, and having computer-executable instructions for performing one of the above methods.

BRIEF DESCRIPTION OF THE DRAWINGS

The invention in the following will be described in detail by referring to exemplary embodiments that are accompanied by figures, in which.

DETAILED DESCRIPTION

Figure 1:
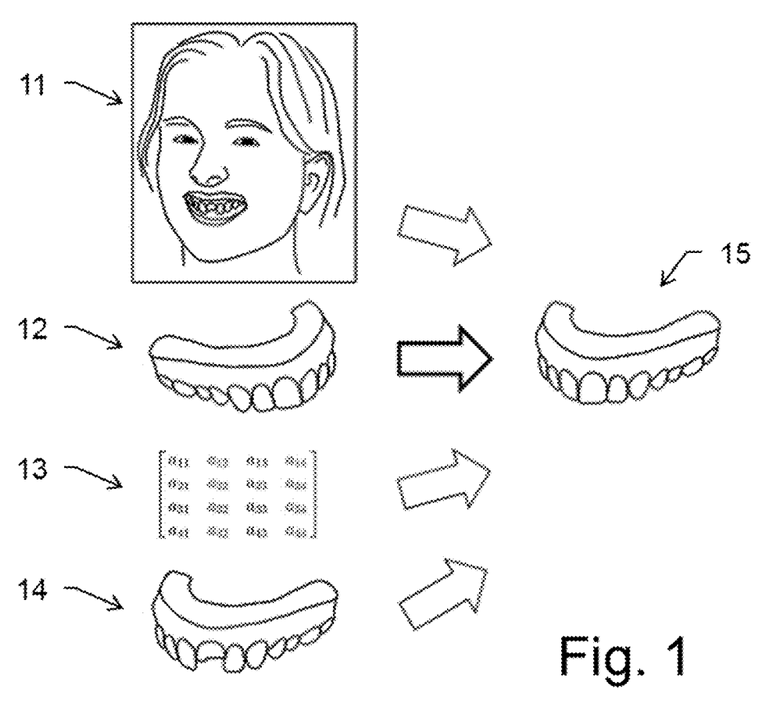
FIG. 1 shows the input and output of an exemplary method for exporting design data of a virtual 3D dental design model from an AR application to a CAD application.

FIG. 1 illustrates an exemplary embodiment of a method for exporting a 3D dental design model 12, bringing it into the coordinate system of a 3D scan of an actual dental situation. For instance, to plan a potential dental treatment, a preliminary dental situation is designed using an augmented reality application (AR app) and then transferred to a CAD software.

As illustrated in FIG. 1, the input comprises:

at least one facial image 11 of a patient where at least a part of the mouth with the actual dental situation is visible, a 3D dental design model 12, e. g. generated by a user using said AR app, an estimated pose 13 of the 3D design model 12 to fit into the image 11, and a 3D scan model 14 of the oral cavity of the face depicted in the image 11 comprising 3D information about the actual dental situation.

The desired output is an aligned 3D dental design model 15, i.e. a three-dimensional model of designed teeth in the same coordinate system as the scan model 14 and matching the scale of the scan model 14.

The 3D scan model 14 may have been created by scanning the oral cavity of the patient or by scanning the impression of the dentition taken by impression trays filled with impression material. Creating the 3D scan model 14 may be part of the method. Alternatively, an existing model may be retrieved. Such three-dimensional model of the dentition of the patient may already be present, e. g. as a basis for developing a digital dental treatment plan, for example by adding artificial teeth or other dental restorations or by modifying the dental situation in another manner, for example by correction of teeth positions. The 3D scan model 14 may comprise the complete oral cavity or only parts thereof.

The 3D design 12 can be a preliminary design. In particular, the 3D design 12 may have a wrong scale or be completely unscaled. The estimated pose 13 can be computed automatically with optional user adjustments in the AR app.

Figure 2:
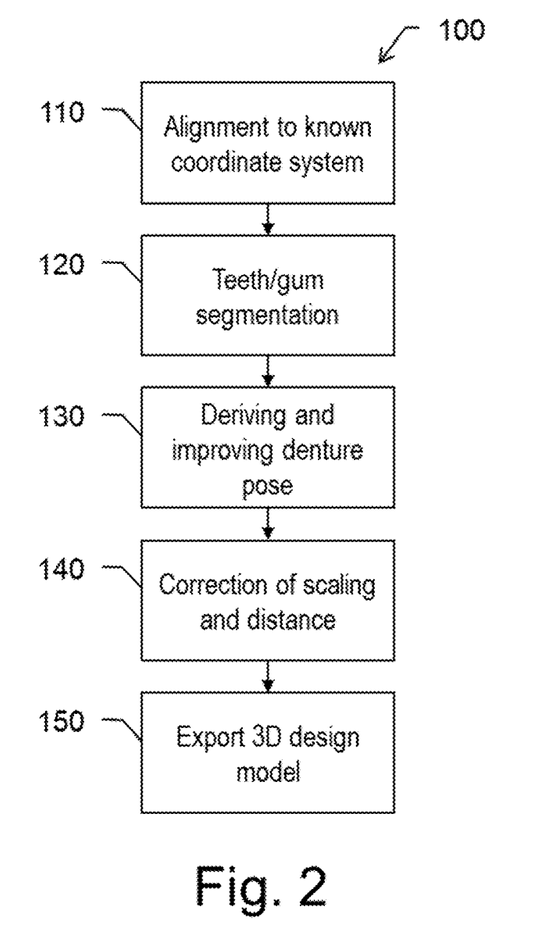
FIG. 2 is a flow chart illustrating an exemplary embodiment of a method for exporting design data of a virtual 3D dental design model from an AR application to a CAD application.
Figure 3:
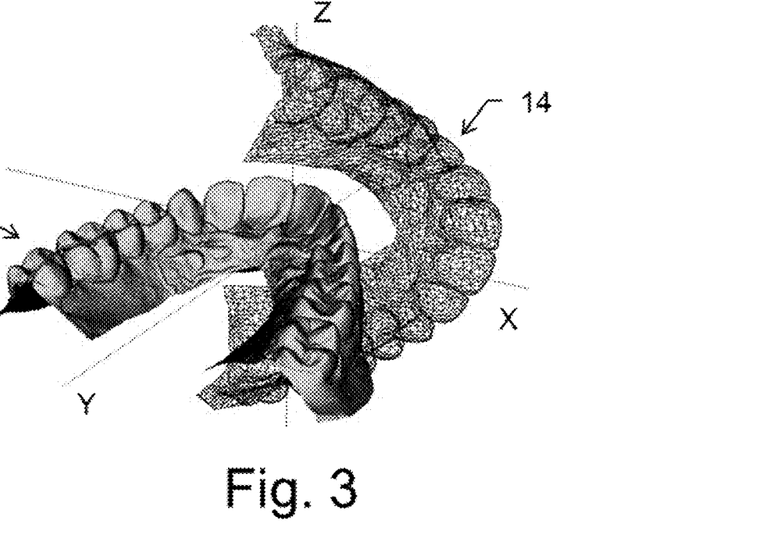
FIG. 3 illustrates the step of aligning the 3D scan to a known coordinate system.

As illustrated by the flow chart of FIG. 2, an exemplary embodiment of the method 100 comprises the following steps:

If the 3D scan model 14 is not already aligned (at least roughly) to the known coordinate system, this alignment is done in step 110. FIG. 3 illustrates, by way of example, the original unaligned position of the 3D scan model 14 and the position of the aligned 3D scan model 14' after having performed said alignment 110. The alignment particularly comprises rotation and translation of the scan model 14. For instance, an automated system can use heuristics or statistical information to find the correct alignment, potentially also correcting the scale e. g. by orders of magnitudes. An auto-alignment, for instance, may comprise the following sub-steps:

1. Shifting a centroid of the 3D scan model 14 to the origin of the coordinate system (intersection of X, Y and Z axis);
2. applying a Principal Component Analysis (PCA);
3. snapping the PCA Y and X axes to the origin Y and X axes;
4. performing a series of flips:
   a. Z-flip with condition that high curvature points are teeth and they have to point into z>0 halfspace,
   b. Z-flip with condition that open edges are on the gum endings and they have to point into z<0 halfspace, and
   c. Y-flip with condition that front teeth half-bounding box points into positive Y axis;
5. Performing translation adjustments including Y offset and occlusal plane.

In step 130, the estimated denture pose 13 is further improved using edge based alignment. The edge based alignment is illustrated in FIGS. 4a-d and disclosed in detail in the applicant's European patent application 18157809.7. This improvement of the pose may be performed automatically with optional fine-tuning by a user.

It may comprise applying inverse transformation to design to keep the design visually at the same position with respect to the image.

The 3D scan model 14 of the denture is rendered by the virtual camera as a two-dimensional image of the denture, wherein the virtual camera is operated assuming an estimated positioning which is estimated to coincide with the positioning of the real camera when recording the image 11 of the patient's face. Preferably, an aperture angle of the camera optical system should to be known. If it is unknown, it can be estimated instead.

Figure 4A:
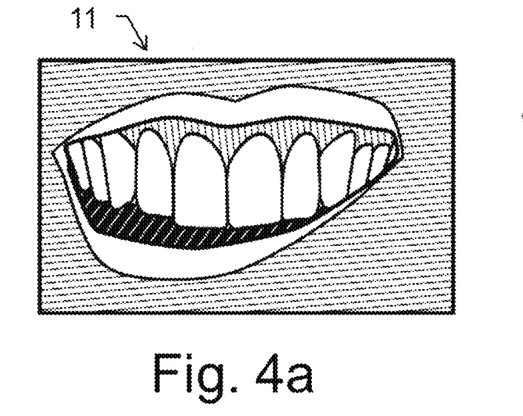
FIGS. 4a-d illustrate edge based alignment as an example for performing the step of improving the denture pose.
Figure 4B:
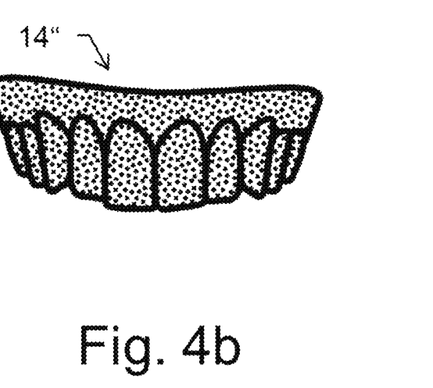
Figure 4C:
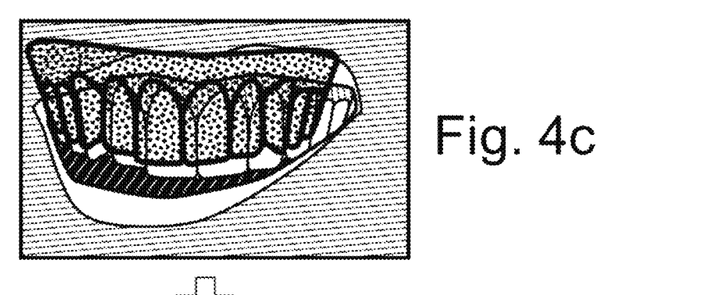
Figure 4D:
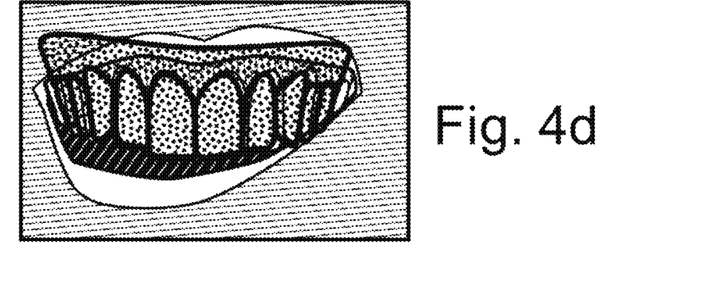

The image 11 of FIG. 4*a* and the rendered image 14″ of the 3D scan model of FIG. 4*b* are then separately processed by carrying out feature detection in a dentition area inside the mouth opening in the respective images 11, 14″ by performing edge detection and/or color-based tooth likelihood determination in the respective images 11, 14″. The image 11 does not have to include the entire face, as the region of the mouth opening is sufficient.

For the detected feature (edges or tooth likelihood) or for each of the detected features (edges and tooth likelihood), this results in two detected feature images (one resulting from the camera image 11 and one from the rendered image 14″) which are then used to calculate a measure of deviation between the detected feature images. Ideally, if the estimated positioning should already coincide with the real positioning of the camera when recording the face image, the measure of deviation would be zero or very small since the detected features (edges or tooth likelihood pattern) would be in identical positions in the two images 11, 14″, and therefore there would be no deviation of the detected features in the two images 11, 14″. However, in practice there will be a certain deviation at the beginning when an estimated position of the virtual camera is used. For this reason, the position of the virtual camera is varied to a new estimated position. This is iteratively repeated in an optimization process to minimize the deviation measure to determine the best fitting positioning of the virtual camera to arrive at the situation depicted in FIG. 4*d*.

Figure 5A:
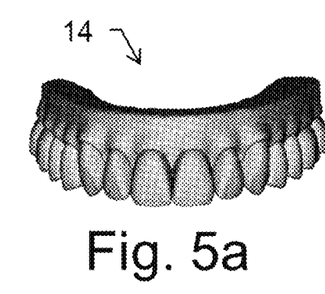
FIGS. 5a-b illustrate the step of segmenting teeth and gum in the 3D scan.
Figure 5B:
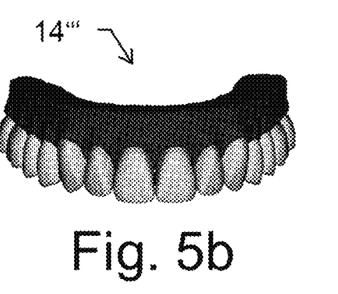

To facilitate the deriving of the pose, optionally, a rough segmentation 120 of teeth and gum can be performed before step 130. This can be done using heuristics with position and surface curvature information or (if available) using heuristics from colour information. Alternatively, if such a segmentation is already comprised in the mesh, that information can be used. This step is also illustrated in FIGS. 5*a-b*, FIG. 5*a* showing a mesh without segmentation (teeth and gum having the same colour) and FIG. 5*b* showing the same mesh after the segmentation 120 of teeth and gum (gum having a darker colour than teeth here).

Optionally, as illustrated in FIGS. 6*a-d*, the scaling and distance can be corrected 140 with the assumption that scan model 14 and dental design model 12 should be at a similar distance to a virtual camera VC. This step solves a potential problem that might occur when an unexperienced user designs the dental design model 12 in an augmented reality application and relates to an apparent size of the model in the AR application. Although the dental design model 12 may look correct, it could be too far in the front (and thus be smaller than intended) or too far behind the scan model 14 (and thus be larger than intended).

Figure 6A:
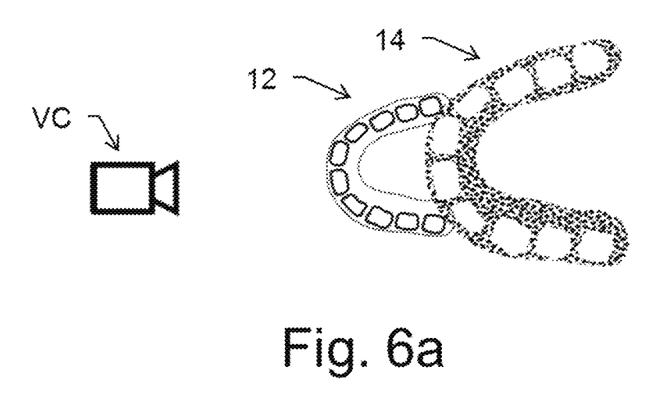
FIGS. 6a-d illustrate the step of correcting a scaling and distance of the 3D dental design model.
Figure 6B:
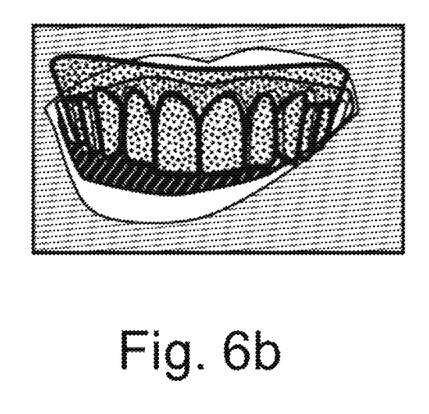
Figure 6C:
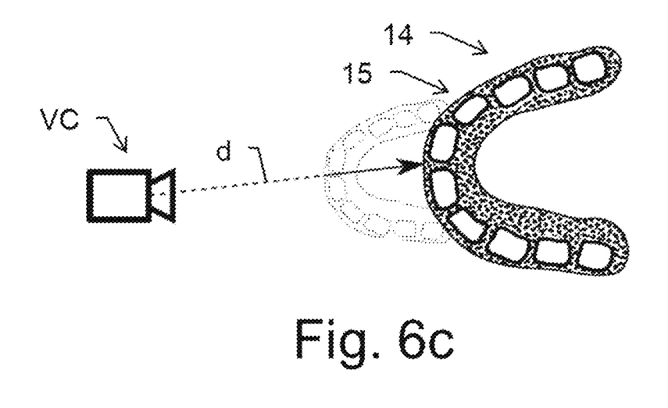
Figure 6D:
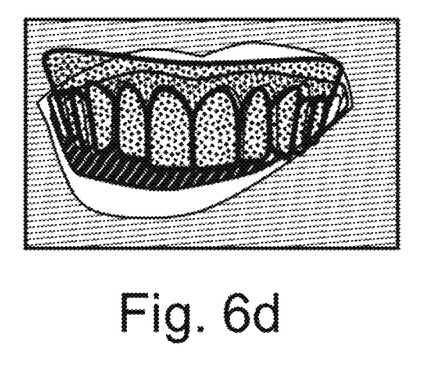

In FIG. 6*a*, the dental design model 12 is much smaller than the scan model 14. As it is also positioned closer to the virtual camera VC, in the augmented reality image of FIG. 6*b*, it appears to have the correct size. After having corrected the distance d to the dental design model 12 (see FIG. 6*c*), the scan model 14 and the dental design model 12 can be aligned so that the aligned dental design model 15 has the correct scale, i.e. so that the apparent size in the image of FIG. 6*d* is the same as in the image of FIG. 6*b*.

Referring to FIG. 2 again, finally, the aligned 3D design model 15 can be exported 150 (e. g. using STL file format) in the same coordinate system as the scan model 14. In particular, the model is exported to be used in a CAD application. However, the model can also be exported for use in other kinds of applications, such as, for instance, in a 3D printer.

Figure 7A:
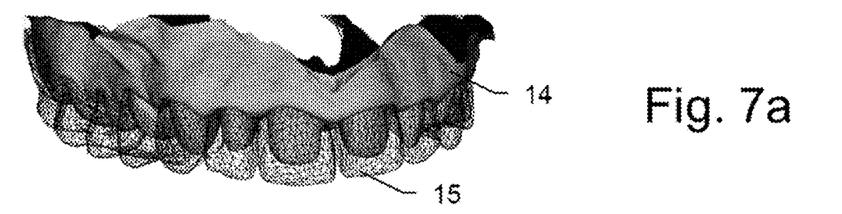
FIGS. 7a-b illustrate the step of exporting the 3D dental design model.
Figure 7B:
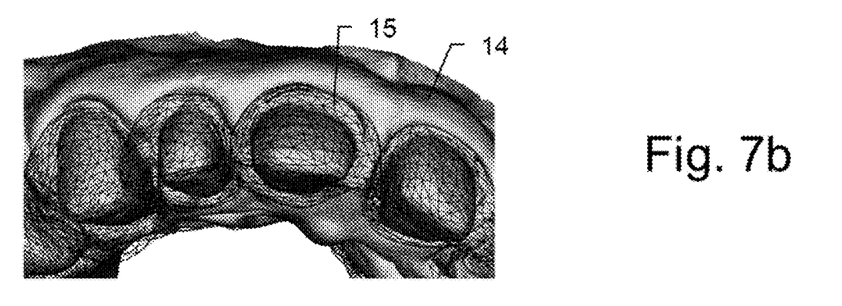

Advantageously, the 3D design model may be exported in the same file together with the scan model. FIGS. 7*a-b* illustrate the result by way of example, where the scan model 14 and the aligned 3D design model 15 are depicted aligned to each other.

In the following, an exemplary embodiment of the method 100 is described by way of equations. A 3D point of the design can be projected onto the image with $$v_{design2D} = P_{cam} \times D_{app} \times M_{app} \times v_{design3D},$$

and the scan can be visualized in the image with:

$$v_{scan2D\_wrong} = P_{cam} \times D_{app} \times A \times v_{scan3D},$$

where:

$P_{cam}$ is a 4×4 camera projection matrix that is computed from the image dimensions and the image field of view;

D is a 4×4 denture pose, a transform that brings a point from denture coordinates to camera coordinates, $D_{app}$ being an estimated 4×4 denture pose from the AR app;

M is a 4×4 design pose, $M_{app}$, being a transformation that the user specified with the user interface relative to $D_{app}$;

$V_{design2D}$ is a point in the image in 2D;

$V_{design3D}$ is a point on the model in 3D in the model coordinate system, i.e. the denture coordinate system;

$V_{scan3D}$ is a vertex of the scan in 3D in an arbitrary coordinate system; and A is an alignment transform that brings the scan model (at least approximately) into the denture coordinate system (step 110).

However, the scan $V_{scan2D\_wrong}$ usually does not fit precisely, as the estimated denture pose $D_{app}$ and the alignment A both are not exact. An improved denture pose $$D_{refined} = D_{app} \times D_{corr}$$

needs to be found, such that the fit is as good as possible:

$$v_{scan2D\_refined} = P_{cam} \times D_{refined} \times A \times v_{scan3D}.$$

$D_{corr}$ can be computed with edge based alignment or defined manually.

According to step 130, with the adjusted denture pose $D_{refined}$, the projection of the design should stay at the same position:

$$v_{design2D} = P_{cam} \times D_{app} \times D_{corr} \times D_{corr}^{-1} \times M_{app} \times v_{design3D}$$

$$v_{design2D} = P_{cam} \times D_{refined} \times M_{refined} \times v_{design3D}$$

with $M_{refined} = D_{corr}^{-1} \times M_{app}$.

There is still an ambiguity in scale and distance from camera. As the true scale of the scan is known, the distance where it matches the image is known, too. Assuming that the distance d1 of the design from the camera should be the same as the distance d2 of the scan from the camera, the distance can be corrected with $T_{dist}$. For the visual result to stay the same, in step 140, the model needs to be scaled by d2/d1 with $T_{scale}$:

$$v_{design2D} = P_{cam} \times D_{refined} \times T_{dist} \times T_{scale} \times M_{refined} \times v_{design3D}.$$

Finally, in step 150, the design can be exported in the same coordinate system and same scale as the scan:

$$v_{design3Dexport}=A^{-1}\times T_{dist}\times T_{scale}\times M_{refined}\times v_{design3D}.$$

Figure 8:
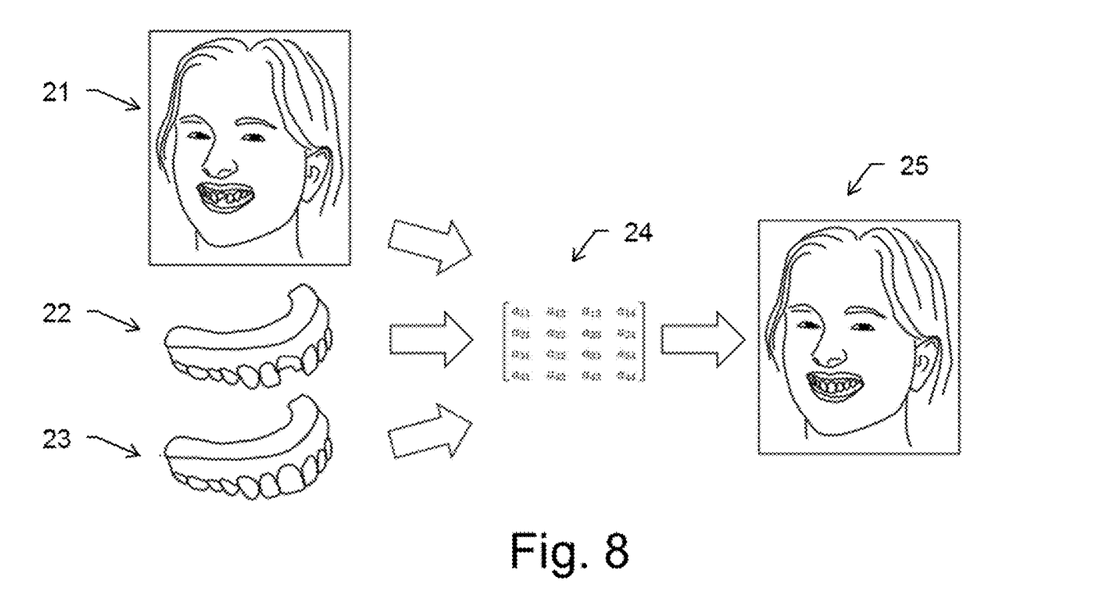
FIG. 8 shows the input and output of an exemplary method for visualizing a 3D dental design model in an AR application.

FIG. 8 illustrates an exemplary embodiment of a method for visualizing an imported 3D dental design model 23 in an AR application, bringing a design resulting from a CAD or simulation (e. g. orthodontics) into a specific pose matching to a facial image 21 for an Augmented Reality overlay. The objective is to display the dental design in the image 21 in the mouth of a person. For instance, to preview a dental situation in the face of a patient, the situation is designed as a dental model using a CAD application and then transferred to an AR application software.

As illustrated in FIG. 8, the input comprises at least one facial image 21 with at least part of the mouth visible, a 3D scan model 22 of the oral cavity, wherein the 3D scan model 22 has a coordinate system that is not necessarily aligned to the coordinate system of the face in the image 21, and the imported 3D dental design model 23, e. g. having been designed previously in a CAD application. The output comprises a pose 24 of the 3D design model 23 corresponding to the image 21 and the corresponding rendered image 25.

The 3D scan 22 as well as the 3D dental design model 23 optionally may comprise colour information and/or a segmentation of teeth and gum.

Figure 9:
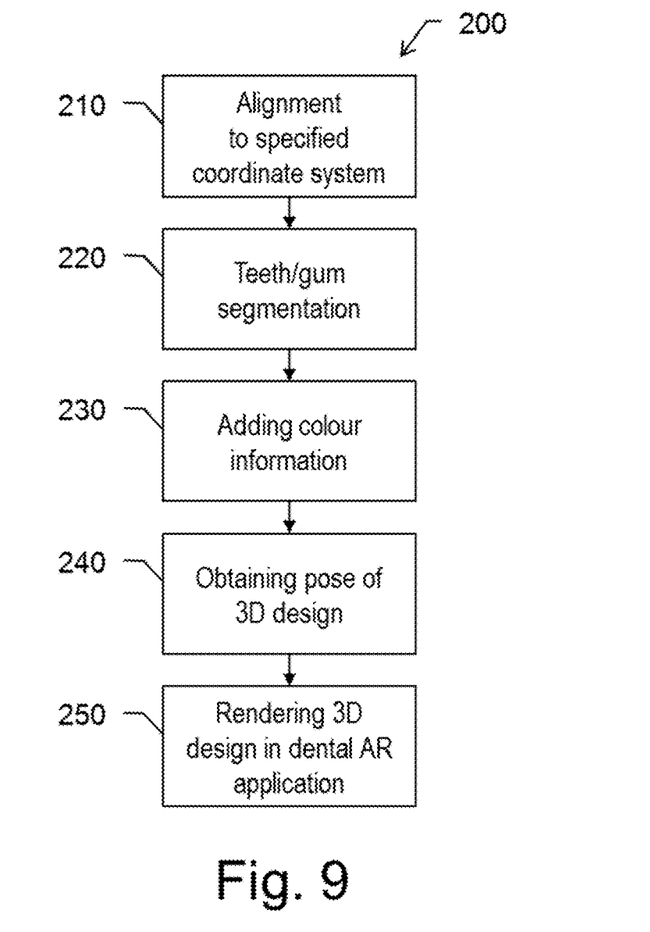
FIG. 9 is a flow chart illustrating an exemplary embodiment of a method for visualizing a 3D dental design model in an AR application.

As illustrated by the flow chart of FIG. 9, an exemplary embodiment of the method 200 comprises the following steps:

In a first step 210, the 3D scan 22 and the 3D design 23 are—at least roughly—aligned to a specified coordinate system. The same transformation is used for both 3D models 22, 23, i.e. both 3D models stay registered relative to each other. The 3D scan 22 and the 3D dental design model 23 optionally can be provided in the same coordinate system. Otherwise, they can be aligned to be in a common specified coordinate system.

A rough segmentation 220 of teeth and gum can then be performed in the 3D scan 22. This can be done using heuristics with position and surface curvature information or (if available) using heuristics from colour information. Alternatively, if such a segmentation is already comprised in the mesh of the 3D scan 22, that information can be used.

Especially if the 3D dental design model 23 does not already have colour information, in step 230 such colour information can be added to the model 23. This can be done either manually, semi- or fully automatically, e. g. using statistical information and heuristics. Colour information is important to let the design model 23 look more realistic in the AR application.

In step 240, the final pose 24 of the 3D design 23 is obtained. After step 210, the pose of the 3D design 23 is already in the specified coordinate system. The final pose 24 may be calculated using pose estimation from the dental AR application. The calculation for instance can be based on information about the segmentation of teeth and gum in the 3D scan 22 and on colour information from the 3D dental design model 23 (i.e. based on the information obtained in previous steps 220 and 230). The final pose 24 optionally can be further improved, e.g. by using a 3D scan for applying edge based alignment as described above with respect to FIGS. 4a-d and disclosed in the European patent application 18157809.7.

In the last step 250, the 3D dental design model 23 is rendered and a 2D representation of the model having the final pose 24 is displayed in the dental AR application, e. g. in the facial image 21 to provide the rendered image 25 as a result.

In an exemplary embodiment, a method for exporting design data of a virtual three-dimensional dental design model is provided. The method includes providing an augmented reality visualizer displaying a dental design model. The design model has a preliminary pose and scale. The dental model is shown in an image of a face and the face image includes at least a portion of a mouth region and a dental situation. A 3D scan model of the dental situation is obtained. The dental situation of the scan model and the dental situation of the image are aligned to obtain a pose of the scan model. The method includes calculating, using a processor, at least one transform to bring the design model and the scan model into a common coordinate system based on the preliminary pose and scale and the pose of the scan model. An export dataset of aligned design data is generated based on the at least one transform. The aligned design data comprises at least one surface geometry of the design model. At least one model may be exported such that both models are aligned in a common coordinate system.

In the context of the present invention, the term "denture" is not necessarily restricted to full dentures but also comprises partial dentures or orthodontic situation/adaptations or dental restorations such as dental prostheses, including crowns, crown lays, veneers, inlays and onlays, bridges, dental implants, implant restorations. Accordingly, the term "dental model" includes all models of dental prostheses as well as the patient situation that could be partial or fully edentulous—such as models of complete and partial dentures—that are used for prosthodontic purposes.

In some embodiments, the present disclosure is implemented using a system having a camera, a processor, an electronic data storage unit, and a display. The camera can be a standard camera, an infrared dot-projection detector, flood illuminator camera, structured-light three-dimensional scanner, standard infrared detector, ultrasonic imaging device, Doppler detector, or any other suitable visualization system capable of capturing information related to a patient's dentition. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image.

In some embodiments, the camera, processor, electronic data storage unit, and digital display are components of a single device. The single device may be a smartphone, tablet, laptop computer, personal digital assistant, or other computing device.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

In some embodiments, the system operates to provide one or more users with a visualization of a virtual dental model of a patient's teeth, which may be altered to visualize the effect of one or more dental or orthodontic alterations. In some embodiments, this allows the one or more users to visualize a "before" dentition image, i.e., the appearance of a patient's dentition prior to a dental or orthodontic procedure, and an "after" dentition image, i.e., a representation of the expected appearance of a patient's dentition after a proposed dental or orthodontic procedure.

In some embodiments, the system operates by capturing information related to a patient's dentition using a camera, creating a model of the patient's dentition on a processor, fitting a model of a proposed post-alteration dentition to the patient's dentition on the processor, coloring the model of the proposed post-alteration dentition to match an expected real post-alteration coloration, and displaying the fitted model of the proposed post-alteration dentition in place of the patient's actual dentition on a display which otherwise shows the patient's actual facial features. The information related to a patient's dentition, the model of the patient's dentition, and the model of the proposed post-alteration dentition may be stored on an electronic data storage unit. In some embodiments, the operations are performed in real-time.

In some embodiments, a user interface is configured such that a user may view the "before" dentition image and the "after" dentition image simultaneously either side-by-side or with a full or partial overlay.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A method (100) for exporting design data of a virtual three-dimensional dental design model (12) from an augmented reality application, the augmented reality application being adapted to visualize the dental design model (12) with a preliminary pose and scale (13) in an image (11) of a face comprising a mouth region with a dental situation, the method comprising:
providing a three-dimensional scan model (14) of the dental situation,
aligning the scan model (14) and the dental situation in the image (11) to obtain a pose of the scan model (14),
calculating, based on the preliminary pose and scale (13) and the pose of the scan model (14), at least one transformation to bring the design model (12) and the scan model (14) into a common coordinate system, in particular wherein the dental design model (12) is brought to a coordinate system of the scan model (14), and
obtaining an aligned design model (15) by
aligning the design model (12) and the scan model in the common coordinate system, and
calculating (140) a corrected scale of the dental design model (12) and applying the corrected scale so that the scale of the aligned design model (15) matches the scale of the scan model (14), wherein calculating (140) the corrected scale comprises calculating a distance of the dental design model (12) to a virtual camera (VC) to match a distance (d) of the scan model (14) to the virtual camera.

2. The method (100) according to claim 1,
characterized by
generating aligned design data based on the transformation, wherein
the aligned design data comprises at least a surface geometry of the design model (12), or
the method comprises obtaining an aligned design model (15) by aligning the design model (12) and the scan model (14) in the common coordinate system and the aligned design data comprises at least a surface geometry of the aligned design model (15).

3. The method (100) according to claim 2, characterized by
exporting (150) the aligned design data to another application, particularly wherein
exporting (150) comprises generating an export file comprising the aligned design data,
the aligned design data is exported (150) in a file together with scan model data related to the scan model (14),
the other application is an external application,
the other application is a computer-aided design application, and/or
the export file is in STL file format.

4. The method (100) according to any one of the preceding claims,
characterized in that
calculating the transformation comprises applying inverse transformation to the dental design model (12) to maintain visually the same position of the dental design model (12) with respect to the image (11).

5. Method (100) according to claim 1,
characterized in that
the method comprises aligning (110) the scan model (14) to a known coordinate system before calculating the transformation, particularly wherein aligning (110) the scan model (14) to the known coordinate system
is performed automatically, using heuristics and/or statistical information, and/or
comprises correcting a scale of the scan model (14), in particular by orders of magnitudes.

6. The method (100) according to claim 1,
characterized in that
a model based alignment is used for aligning the dental situation of the scan model (14) and the dental situation in the image (11), the model based alignment comprising at least:
estimating a position of a camera used for capturing the image (11) relative to the face in the image (11) during recording of the image,
rendering a two-dimensional image (14") of the scan model using a virtual camera (VC) processing the scan model (14) at the estimated position, and
carrying out feature detection in the mouth region of the image (11) recorded by the camera and in the rendered image (14") by performing edge detection and/or a colour-based tooth likelihood determination in the respective images (11, 14") and forming a detected feature image for each detected feature.

7. The method (100) according to claim 1,
characterized in that
the dental design model (12) is designed or modified by a user using the augmented reality application, in particular wherein the method comprises designing or modifying the dental design model (12) using the augmented reality application.

8. A computer programme product comprising programme code which is stored on a machine-readable medium, the machine-readable medium comprising computer instructions executable by a processor, which computer instructions cause the processor to perform the method according to claim 1.

9. A method (200) for visualizing a three-dimensional dental design model (23) in an augmented reality application wherein the method comprises:
   providing the dental design model (23), a three-dimensional scan model (22) of a dental situation and an image (21) of a face comprising a mouth region with the dental situation,
   determining (240) a pose (24) for the dental design model (23) based on the image (21) and on a relative transformation from the scan model (22) to the dental design model (23),
   rendering (250) the dental design model (23) in the image (11) with the determined pose (24), and
   wherein determining (240) the pose (24) comprises using a model based alignment for aligning the dental situation of the scan model (22) and the dental situation in the image (21), the model based alignment comprising at least:
      estimating a position of a camera used for capturing the image (21) relative to the face in the image (21) during recording of the image,
      rendering a two-dimensional image of the scan model (22) using a virtual camera (VC) processing the scan model (22) at the estimated position, and
      carrying out feature detection in the mouth region of the image (21) recorded by the camera and in the rendered image of the scan model (22) by performing edge detection and/or a colour-based tooth likelihood determination in the images and forming a detected feature image for each detected feature.

10. The method (100) according to claim 9, characterized in that
the dental design model (23) is provided to the augmented-reality application by a computer-aided design application or orthodontic simulation, particularly wherein
   the dental design model (23) is designed or modified by a user using the computer-aided design application or orthodontic simulation, and/or
   the method comprises designing or modifying the dental design model (23) using the computer-aided design application or orthodontic simulation.

11. The method (100) according to claim 9, characterized by
aligning (210) the dental design model (23) and the scan model (22) to a specified coordinate system, particularly wherein
   the same transformation is used for the dental design model (23) and the scan model (22), and/or
   the dental design model (23) and the scan model (22) stay registered relative to each other.

12. The method (100) according to claim 9, characterized in that
colour information is added (230) to the dental design model (23), and the dental design model (23) is rendered with the added colour information, particularly wherein the colour information is added semi- or fully automatically using statistical information and/or heuristics.

13. The method (100) according to claim 9, characterized in that
a segmentation (120, 220) of teeth and gum in the scan model (14, 22) is performed using colour information of the scan model and/or using heuristics with position and surface curvature information from the scan model, wherein determining (130, 240) the pose of the scan model (14, 22) is based on the segmentation.

* * * * *